(12) United States Patent
Mirzabekov et al.

(10) Patent No.: US 7,846,656 B2
(45) Date of Patent: Dec. 7, 2010

(54) COMPOSITION FOR POLYMERIZING IMMOBILIZATION OF BIOLOGICAL MOLECULES AND METHOD FOR PRODUCING SAID COMPOSITION

(75) Inventors: Andrei Darievich Mirzabekov, Moscow (RU); Alla Jurievna Rubina, Moscow (RU); Sergei Vasilievich Pankov, Samara (RU)

(73) Assignee: Institut Molekulyarnoi Biologii IM.V.A. Engelgardta Rossiiskoi Akademii Nauk, Moscow (RU)

( * ) Notice: Subject to any disclaimer, the term of this patent is extended or adjusted under 35 U.S.C. 154(b) by 1414 days.

(21) Appl. No.: 10/450,641

(22) PCT Filed: Oct. 16, 2001

(86) PCT No.: PCT/RU01/00420

§ 371 (c)(1),
(2), (4) Date: Oct. 28, 2003

(87) PCT Pub. No.: WO03/033539

PCT Pub. Date: Apr. 24, 2003

(65) Prior Publication Data

US 2004/0053298 A1    Mar. 18, 2004

(51) Int. Cl.
*C12Q 1/68*    (2006.01)
(52) U.S. Cl. .......................................................... 435/6
(58) Field of Classification Search ........................ None
See application file for complete search history.

(56) References Cited

U.S. PATENT DOCUMENTS

| 5,412,087 | A |   | 5/1995  | McGall et al. |
| 5,476,653 | A | * | 12/1995 | Pitt et al. ................... 424/78.3 |
| 5,574,142 | A |   | 11/1996 | Meyer, Jr. et al. |
| 5,660,702 | A | * | 8/1997  | Starr ........................... 204/469 |
| 5,837,860 | A |   | 11/1998 | Anderson et al. |
| 5,932,711 | A | * | 8/1999  | Boles et al. ................ 536/22.1 |
| 5,981,734 | A | * | 11/1999 | Mirzabekov et al. ....... 536/25.3 |
| 6,682,893 | B2| * | 1/2004  | Taylor et al. .................. 435/6 |

FOREIGN PATENT DOCUMENTS

| RU | 2157385      | 10/2000 |
| RU | 99127744/04  | 9/2001  |
| WO | 0114425      | 3/2001  |

OTHER PUBLICATIONS

English translation of claims of RU 2157385, Dated Oct. 10, 2000.
English translation of claims of RU 99127744/04, Dated Sep. 10, 2001.
Shur, A. M. *High-Molecular Compounds*, Moscow: Visshaya Shkola. 1981. pp. 82-85, 104-107, 112-113.
Good, A. and J.C.J. Thynne. "The Thermal Decomposition of Tetramethyltetrazen and the Addition of Dimethylamino-radicals to Ethylene", *J. Chem. Soc.*, (1976), pp. 684-685.
Michejda, Christopher J. and Dwane H. Campbell. "Radical Catalyzed Epoxidation with Oxygen", *J. American Chemical Society*, (1976), 98(21): 6728-6729.
Michejda, Christopher J. and Dwane H. Campbell. "Amphoteric Amino Radicals", *Tetrahedron Letters*, (1977), No. 6: 577-580.
Sutherland, I.O., Editor. *Comprehensive Organic Chemistry: The Synthesis and Reaction of Organic Compounds. vol. 2: Nitrogen Compounds*. Pergamon Press. 1982.
Yasunaga, S. et al. "Different contribution of HLS-DR and -DQ genes in susceptibility and resistance to insulin-dependent diabetes mellitus (IDDM)", *Tissue Antigens*, (1996), 47: 37-48.
Proudnikov, Dmitri et al. "Immobilization of DNA in Polyacrylamide Gel for the Manufacture of DNA and DNA-Oligonucelotide Microchips", *Analytical Biochemistry*, (1998), 259: 34-41.

* cited by examiner

*Primary Examiner*—Christopher M. Babic
(74) *Attorney, Agent, or Firm*—Ladas & Parry LLP

(57) ABSTRACT

The invention refers to the field of molecular biology and bio-organic chemistry and deals with a composition for immobilization in polymer carriers of oligonucleotides, proteins, nucleic acids or any other molecules, which structure comprises active groups, including amino- or sulfhydryl groups, as well as a method for immobilization of various molecules including oligonucleotides, proteins, nucleic acids or any other molecules which structure comprises active groups, including amino- or sulfhydryl groups, consisting of a porous polymer being obtained on the basis of the composition claimed under conditions of addition or substitution reaction (radical, nucleophilic, or electrophilic nature, etc.) during synthesis of polymer by photo- and chemical initiated polymerization.

The composition claimed, as well as the method of immobilization of molecules in a polymer carrier using these compositions, may be used in various applications including microchips manufacturing that use is made of molecular biology on DNA sequencing and mapping, on detection of mutations and a whole range of medical applications.

25 Claims, 2 Drawing Sheets

COMPOSITION FOR POLYMERIZING IMMOBILIZATION OF BIOLOGICAL MOLECULES AND METHOD FOR PRODUCING SAID COMPOSITION

FIELD OF INVENTION

The invention refers to the field of molecular biology and bio-organic chemistry and deals with a composition for immobilization of in polymer carriers of oligonucleotides, proteins, nucleic acids or any other molecules, which structure comprises active groups, including amino- or sulfhydryl groups, as well as a method for immobilization of various molecules including oligonucleotides, proteins, nucleic acids or any other molecules which structure comprises active groups, including amino- or sulfhydryl groups, consisting of a porous polymer being obtained on the basis of the composition claimed under conditions of addition or substitution reaction (radical, nucleophilic, or electrophilic nature, etc.) during synthesis of polymer by photo- and chemical initiated polymerization.

The composition claimed, as well as the method of immobilization of molecules in a polymer carrier using these compositions, may be used in various applications including microchips manufacturing that use is made of molecular biology on DNA sequencing and mapping, on detection of mutations and a whole range of medical applications.

BACKGROUND OF INVENTION

It is known in the art that cyclic compounds, or compounds containing two or more multiple bonds, are used for polymer synthesis by method of radical polymerization, regardless of the method initiation thereof (photo-, thermal, radiation, or chemical initiation) [1].

[1] А. М. Шур, Высокомолекулярныесоединения (High-Molecular Compounds), М: Высшаяшкола, 1981, с. 82-143.

The reaction proceeds by radical chain mechanism via initiation, chain growth, and chain termination steps. Such a nature of the radical polymerization provides favourable conditions for insertion in the polymer structure of various molecules including oligonucleotides, proteins, nucleic acids, which structure comprises amino-, sulfhydryl or other active groups. There are at least two possible paths of insertion:

1. Molecules, which structure comprises amino-, sulfhydryl or other active groups, take part in chain transfer reaction to form aminyl, sulfanyl, or other active radicals. These radicals are capable to insert in the polymer structure both on chain growth step and on chain termination step under intermolecular recombination [2,3,4].

[2] A. Good and J. C. Thynne, J. Chem. Soc., 1967, p. 684.

[3] C. J. Micheida and D. H. Campbel, J. Amer. Chem. Soc., 1976, 98, p. 6728.

[4] C. J. Micheida and D. H. Campbel, Tetrahedron Letters, 1977, p. 577.

2. Molecules, which structure comprises amino-, sulfhydryl, or other active groups, take part in reaction of nucleophilic addition to unsaturated compounds [5] that present on various polymerization steps, namely with initial monomers, growing unsaturated macroradicals, and unsaturated macromolecules.

[5] Общаяорганическаяхимия(General Organic Chemistry), T. (v.) 3, Азотсодержащиесоединения(Nitrogen-Containing Compounds), H. K. Кочетков(Ed.), М: Химия, 1982, с. 61-62.

SUMMARY OF INVENTION

The essence of invention consists in that there are provided:

A composition for immobilization of molecules including oligonucleotides, proteins, and nucleic acids, which structure comprises active groups including amino- and/or sulfhydryl groups in polymer carriers (polymers) under conditions of addition or substitution reaction (radical, nucleophilic, electrophilic etc.) during synthesis of polymer by photo- and chemical initiated polymerization; and A method for immobilization of molecules including oligonucleotides, proteins, and nucleic acids, which structure comprises active groups including amino- and/or sulfhydryl groups in polymer carriers (polymers) under conditions of addition or substitution reaction (radical, nucleophilic, electrophilic etc.) during synthesis of polymer by photo- and chemical initiated polymerization.

The present composition and method of immobilization of various molecules in a polymer carrier using this composition will be used in various applications including a microchip manufacturing.

For immobilization of molecules which structure comprises active groups including amino- or sulfhydryl groups in polymer carriers, there is provided a composition of the following formula:

$$K = A^a + B^b + C^c + D^d + E^e + F^f$$

wherein

K is a composition;

A is acrylamide, methacrylamide, N-[tris(hydroxymethyl)methyl]acrylamide, 2-hydroxyethylmethacrylate or the monomer based on derivatives of acrylic, methacrylic, cinnamic, crotonic, vinylbenzoic or other unsaturated acids;

B is N,N'-methylenebisacrylamide, N,N'-1,2-dihydroxyethylenebisacrylamide, polyethyleneglycol diacrylate, a mixture thereof or a symmetric or asymmetric cross-linking agent based on derivatives of acrylic, methacrylic, cinnamic, crotonic, vinylbenzoic or other unsaturated acids;

C is an oligonucleotide, nucleic acid, protein or another molecule bearing an active group including an amino- or sulfhydryl group;

D is glycerol, sucrose, polyhydric alcohols, or another high-boiling compound;

E is water, N,N-dimethylformamide, dimethylsulfoxide, and other polar and non-polar solvents;

F is ammonium persulfate, potassium persulfate, methylene blue, fluorescein, N,N,N',N'-tetramethyl ethylenediamine, hydrogen peroxide, 4-(N,N-dimethylamino)pyridine, triethylamine, acetone or any other initiator for chemical or photo-initiated polymerization.

a, b, c, d, e, f are percentages of any ingredient in the composition (for solids X=m/v×100% and for liquids X=v/v×100%).

$3 \leq a+b \leq 40\%$; $0 \leq c \leq 10\%$; $0 \leq d \leq 95\%$; $0 \leq e \leq 95\%$, $0 \leq f \leq 90\%$.

Along with polymers of another application, the composition as indicated above is proposed to use for manufacturing oligonucleotide, protein, DNA (RNA), and other biological microchips.

The present composition for manufacturing biological microchips will make use of the following ingredients:

Monomers Composing the Basis of Polymer Carrier Being Formed

As monomers forming a linear polymer, there are to be used derivatives of acrylic, methacrylic, cinnamic, vinylbenzoic, crotonic or other unsaturated acids including their esters and amides, for example, acrylamide, methacrylamide, N-[tris(hydroxymethyl)methyl]acrylamide, 2-hydroxyethylmethacrylate, methylmethacrylate etc.

As cross-linking agents for forming the three-dimensional gel structures, there are used compounds, which structure comprises two or more unsaturated fragments from which at least one is active in the addition or substitution reactions (radical, nucleophilic, electrophilic, etc.), for example, N,N'-methylenebisacrylamide, N,N'-methylenebismethacrylamide, N,N'-1,2-dihydroxyethylenbis acrylamide, etc. or symmetric and asymmetric esters, amides, and mixed derivatives of acrylic, methacrylic, cinnamic, crotonic, vinylbenzoic, or other unsaturated acids.

Total content of monomer forming the linear polymer, (A), and cross-linking agent, (B), in the composition is in the range of 3-40% (3<T<40), and their ratio being in the range of 97:3-60:40% (3<C<40).

Polymers having a predetermined pore size are to be prepared by varying the combinations and ratios of monomers.

Oligonucleotides, Proteins, Nucleic Acids, which Structure Comprises Active Groups Including Amino- and Sulfhydryl Groups It is necessary for immobilization of oligonucleotides, nucleic acids, proteins or other molecules in the polymer carrier during its synthesis on chemical or photochemical initiation that molecules being immobilized comprise active groups which are capable to go into addition or substitution reactions (radical, nucleophilic, electrophilic, etc.) with fragments of polymer being formed during its synthesis. In particular, amino-H sulfhydryl groups are provided as such active groups.

Oligonucleotides, which structure comprises amino- or sulfhydryl groups, are prepared under conventional conditions of phosphoramidite chemistry using commercially available phosphoramidites.

DNA fragments having amino- or sulfhydryl groups are prepared under conditions of symmetric or asymmetric polymerase chain reaction using a synthetic primer bearing terminal amino- or sulfhydryl groups [6] or by amination of DNA fragments using a procedure as described in a reference [7].

[6] Yasunaga, S., Kimura, A., Hamaguchi, K., Ronningen, K. S., and Sasazuki, T., Tissue Antigens., 1996, 47., 37-48.

[7] Proudnikov D, Timofeev E, Mirzabekov A., Anal Biochem. 1998, 15; 259(1), P. 34-41.

For immobilization, protein molecules having free amino-, sulfhydryl, and other active groups make use of native form, without additional modifications.

In the compositions, the content of molecules having active groups (C) is varied in the range of $0 \leq c \leq 10\%$.

Medium Used for Immobilization of Molecules Having Amino- and Sulfhydryl Groups in Polymer Carriers.

As a medium for a polymerizing immobilization of molecules, there are provided water, aqueous solutions of polyvinyl alcohol, sucrose, dimethylformamide, dimethylsulfoxide or other polar water soluble and non-polar compounds as well as anhydrous solutions of dimethylsulfoxide, dimethylformamide, formamide, etc. In the compositions, water content (E) is varied in the range of 0-95% (v/v), and a high-boiling compound (D) is of 0-95% (w/v; v/v).

Various compounds may be added in solutions for polymerization, for example, glycerol to produce compositions of various viscosities that allows varying a size of microchip gel elements under a pin robot diameter fixed.

Initiators for Chemical and Photo-Initiation

To initiate the radical polymerization during synthesis of polymer carrier, there are proposed to make use of initiators and polymerization promoters soluble in water and organic media, namely: ammonium persulfate, potassium persulfate, hydrogen peroxide, ferrous salts, N,N,N',N'-tetramethyl ethylenediamine, triethylamine, benzoyl peroxide, azobisisobutyric acid dinitrile, 4-(N,N-dimethylamino)pyridine, acetone, methylene blue, fluorescein, etc.

Monomers Covalently Attached to a Glass Surface

For modification of a glass surface with the purpose of covalent bonding a polymer carrier to the surface, there are provided the following reagents: 3-trimethoxysilylpropyl methacrylate, 3-trimethoxysilylpropyl methacrylamide, 3-trimethoxysilylpropyl acrylamide, 3-glicidyloxypropyl trimethoxysilane.

Such a set of modifying agents makes it possible to form a reliable bonding a polymer to a glass over a broad range of medium pH (2-12) and of temperature (−10° C.-+100° C.).

Various combinations of composition ingredients allow obtaining polymer carriers which porosity may change over a broad range that makes it possible to use these carriers in many applications, particularly for biochip manufacturing.

An additional aspect of the present invention is a method for immobilization of molecules including oligonucleotides, proteins, and nucleic acids, which structure comprises active groups consisting of linear or three-dimensional porous polymer that is obtained on the basis of composition of formula:

$$K = A^a + B^b + C^c + D^d + E^e + F^f$$

wherein:

K is a composition;

A is acrylamide, methacrylamide, N-[tris(hydroxymethyl)methyl]acrylamide, 2-hydroxyethylmethacrylate or another monomer based on derivatives of acrylic, methacrylic, cinnamic, crotonic, vinylbenzoic or other unsaturated acids;

B is N,N'-methylenebisacrylamide, N,N'-1,2-dihydroxyethylenebisacrylamide, polyethyleneglycol diacrylate, a mixture thereof, or symmetric or asymmetric cross-linking agent based on derivatives of acrylic, methacrylic, cinnamic, crotonic, vinylbenzoic or other unsaturated acids;

C is an oligonucleotide, nucleic acid, protein, or another molecule bearing an active group including amino- or sulfhydryl groups;

D is a glycerol, sucrose, polyhydric alcohol, or another high-boiling compound;

E is water, N,N-dimethylformamide, dimethylsulfoxide or other polar and non-polar solvents;

F is ammonium persulfate, potassium persulfate, methylene blue, fluorescein, N,N,N',N'-tetramethylethylene diamine, hydrogen peroxide, 4-(N,N-dimethylamino)pyridine, triethylamine, acetone, or any other initiator for chemical or photo-initiating polymerization.

a, b, c, d, e, f are percentages of any ingredient in the composition (for solids X=m/v×100% and for liquids X=v/v×100%).

$3 \leq a+b \leq 40\%$;  $0 \leq c \leq 10\%$;  $0 \leq d \leq 95\%$;  $0 \leq e \leq 95\%$, $0 \leq f \leq 90\%$.

For purposes of the present invention, the polymer is preferably obtained by polymerization of (A+B) mixtures using combinations of acrylamide, methacrylamide, N-[tris(hydroxymethyl)methyl]acrylamide, N,N'-methylenebisacrylamide, N,N'-(1,2-dihydroxyethylenebisacrylamide, polyethyleneglycol diacrylamide, or other unsaturated compounds.

It is preferred where molecules including oligonucleotides, proteins, and nucleic acids, which structure comprises active groups including amino- and/or sulfhydryl groups, react with fragments of a polymer carrier (polymer) being formed during its synthesis under conditions of addition or substitution reactions (radical, nucleophilic, electrophilic, etc.) on photo- or chemical initiated polymerization.

Moreover, oligonucleotides, which comprise active groups including amino- and/or sulfhydryl groups, aminated DNA, DNA with sulfhydryl group inserted as well as proteins, are not subjected to a modification before the immobilization process.

A method is further specified in that the immobilization of proteins is performed in polymer carrier either by sulfhydryl groups, or by amino-groups, or by third functionality of aminoacids.

A method is further specified in that the immobilization of oligonucleotides is performed in polymer carrier either by 5'-terminal of oligonucleotide or by 3'-terminal of oligonucleotide.

The method of present invention is further specified in that a polymer layer formed is covalently bonded to a substrate or the covalent bonding to said substrate is absent.

In this case, the polymer layer formed on a substrate is a three-dimensional gel.

The polymer layer formed on a substrate is further a compact continuous layer.

Additionally, the polymer layer as formed on substrate is divided by empty spaces into some cell and each cell will comprise (or not comprise) macromolecules immobilized, and macromolecules being immobilized in various cells will have different nature and properties.

The cell as mentioned above forms the regular one- or two-dimensional structure (phase).

The application of the polymerization mixture on substrate is preferably carried out by using an automatic device (robot) which is equipped with one or more microdispensers, and said microdispensers will be a pin type microdispensers or contactless microdispensers of jet type. Moreover, the method will make use of several microdispensers forming a regular structure.

According to the present invention, the method envisages that before polymerization, one or more substrates including some droplets of composition are hold at a sealed container which comprises the same composition mixture in amounts more than two times exceeding the total amount of the polymerization mixture as supported on substrate.

Moreover, one or more substrates including supported droplets of composition, before and during polymerization, are placed into the sealed container under oxygen free inert atmosphere with controlled humidity.

According to the present method, said container is filled with one of the following gases: $N_2$, Ar, $CO_2$, and gaseous medium being continuously or periodically restored in the container with substrates.

BRIEF DESCRIPTION OF DRAWINGS

The invention is illustrated by using drawings wherein.

Oligonucleotide immobilized (C=130 pmol/µl):

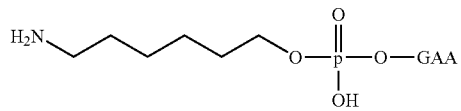

Hybridized oligonucleotide labeled with fluorescent agent:
5'-CTCAGTTC-TexRed (1 µM, IM NaCl). Gels for immobilization:
A{methacrylamide:N,N'-methylenebisacrylamide-T5%, C5%};
B{acrylamide:N,N'-methylenebisacrylamide-T5%, C5%}.

Figure 2:
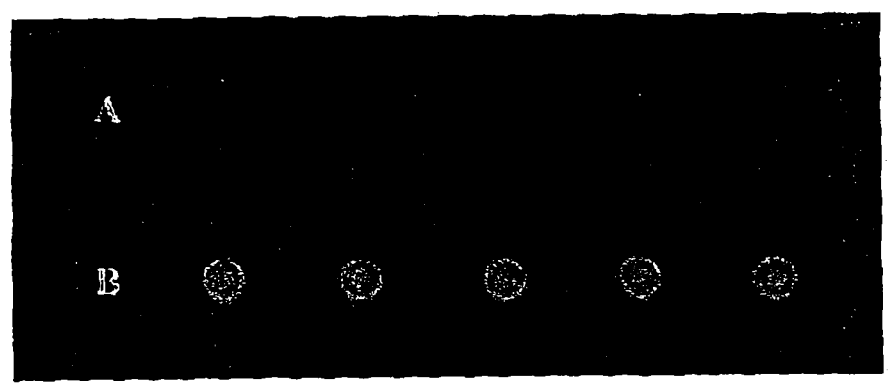

FIG. 2 shows the immobilization of DNA bearing amino- or sulfhydryl groups on a modified glass.

Gels for DNA immobilization: methacrylamide:N,N'-methylenebisacrylamide-T5%, C5%; DNA immobilized (C=1× $10^{-3}$ g/mL): separated from a calf's thymus and subjected to an amination procedure by a protocol as disclosed in reference [4];

Hybridized oligonucleotide labeled with fluorescent agent:
5'-CTCAGTTC-TexRed (1 µM, IM NaCl). A and B are gels which do not comprise or comprise DNA immobilized, correspondingly.

Figure 3:
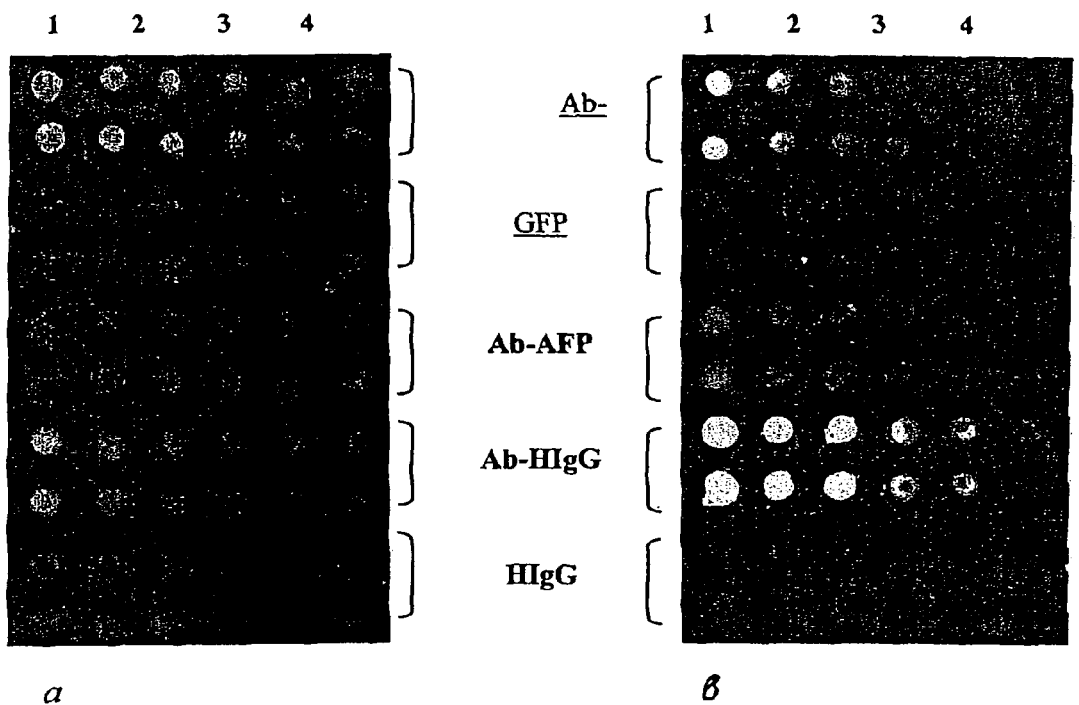

FIG. 3 illustrates an immunoassay on the microchip. The microchip contains immobilized monoclonal antibodies to the green fluorescent protein (Ab-GFP), to α-fetoprotein (Ab-AFP), to human immunoglobulin G (Ab-HIgG), and to human immunoglobulin G (HIgG). The antibody concentrations in the gel are as follows, µg/mL: 630 (series 1), 315 (series 2), 210 (series 3), 130 (series 4), 60 (series 5), 40 (series 6). Antibodies have been developed with the green fluorescent protein (a) and by antibodies to fluorescein labeled HIgG (b).

The invention will be further explained by using examples to illustrate the preferred embodiments of invention. These examples should not to be construed as a limitation of the scope of invention. Persons skilled in the art will make numerous improvements which are also entered in the scope of claims of the present invention as set forth in the claims.

EXAMPLES

Example 1

Immobilization of Oligonucletides Comprising Aliphatic Amino-Group in a Polymer Carrier An aqueous solution of oligonucleotide (2.3 µL, C=1 nmol/µL) and glycerol (6.45 µL) are added to a solution of methacrylamide and N,N'-methylenebisacrylamide in 3M aqueous solution of N,N,N',N'-tetramethylethylene diamine (1.25 µL, 40% (m/v), 19:1). The mixture is thoroughly stirred. The solution is applied by using robot "GMS 417 Arraer" on a glass treated with Bind-Silane. A block of droplets obtained is exposed to ultra-violet rays (λ=312 nm, 30 min, T=55° C.) under dry argon atmosphere, washed with water (4 h, T=60° C.), and dried in a dust-free air (T=25° C.). This example makes use of composition of the following formula: A—methacrylamide, B—N,N'-methylenebisacrylamide, C—oligonucleotide, D—glycerol, E—water, F—N,N,N',N'-tetramethylethylene+diamine, a+b=5.00%, c=0.0006%; d=65.00%; e=20.00%, f=10.00%.

Oligonucleotide microchip obtained is used to perform a hybridization, PCR, etc.

Figure 1:
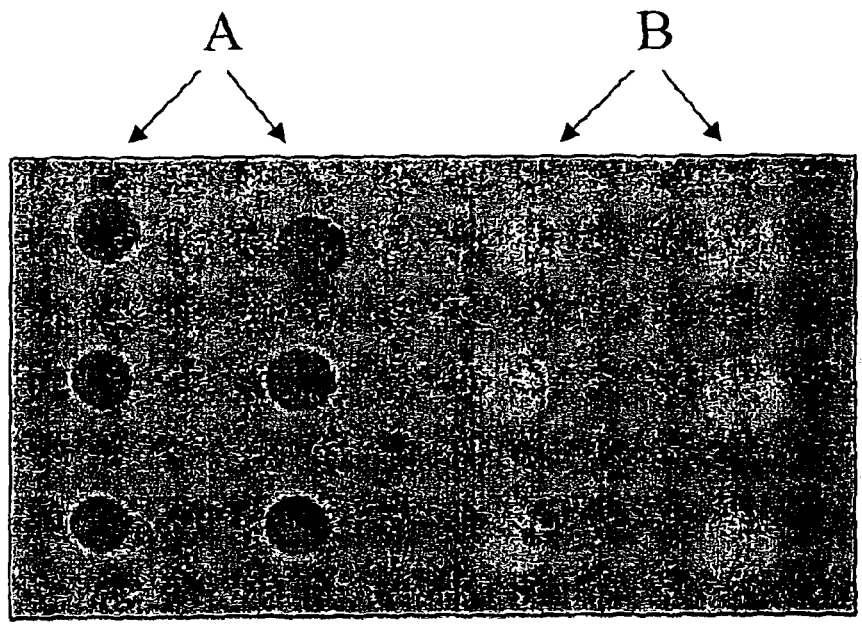
FIG. 1 shows the immobilization scheme for oligonucleotide having a terminal amino-group on a modified glass.

FIG. 1 shows a result of hybridization on oligonucleotide microchip as obtained by the foregoing procedure.

Example 2

Immobilization of Aminated DNA in a Polymer Carrier

The procedure used is as set forth in example 1.

For immobilization, DNA is used as separated from a calf's thymus and aminated by a protocol as disclosed in reference [4]. DNA concentration in the polymerization mixture is of C=1 mg/mL. This example makes use of composition of the following formula: A—methacrylamide, B—N,N'-methylenebisacrylamide, C—DNA, D—glycerol, E—water, F—N, N,N',N'-tetramethylethylene diamine, a+b=5.00%, c=0.00023%; d=65.00%; e=20.00%, f=10.00%.

FIG. 2 shows a result of hybridization on DNA-microchip as obtained by the foregoing procedure.

Example 3

Immobilization of Protein in a Polymer Carrier

The procedure used is as set forth in example 1.

A solution of native form protein in a borate buffer (pH 8.3) is added to a solution of polymerization mixture. The protein concentration in the polymerization mixture is of C=630 µg/mL. The mixture is thoroughly stirred. The solution is applied by using robot "GMS 417 Arraer" on a glass treated with Bind-Silane. A block of droplets obtained is exposed to ultra-violet rays (λ=312 nm, 40 min, T=27° C.) under dry argon atmosphere. The protein microchips are further washed with a phosphate brine buffer (0.01 M, pH 7.0) containing 0.1% Tween 20 then hold for 1 h in the phosphate brine buffer (0.01M, pH 7.0) containing both 1% BSA and 5% of sucrose, and used for performing analyses of various types.

This example makes use of composition of the following formula: A—methacrylamide, B—N,N'-methylenebisacrylamide, C—DNA, D—glycerol, E—water, F—N,N,N',N'-tetramethylethylene diamine, a+b=5.00%, c=0.0001%; d=65.00%; e=20.00%, f=10.00%.

FIG. 3 illustrates results of an immunoassay on the microchip.

The invention claimed is:

1. A method for immobilizing oligonucleotide, nucleic acid and/or protein molecules bearing an active aliphatic amino, an active aliphatic sulfhydryl group or both, in a polymer carrier said method comprising reacting active groups of molecules with a radical of a polymer or monomer during polymerization.

2. A method according to claim 1, wherein the polymer carrier is formed by polymerization of a composition comprising $$K=aA+bB+cC+dD+eE+fF$$

wherein K is the composition;

A is a monomer selected from the group consisting of acrylamide, methacrylamide, N-[tris(hydroxymethyl)methyl]acrylamide, 2-hydroxyethylmethacrylate, methylmethacrylate, and other monomer based on derivatives of unsaturated acids selected from the group consisting of acrylic, methacrylic, cinnamic, crotonic, and vinylbenzoic acid;

B is a symmetric or asymmetric cross-linking agent based on derivatives of unsaturated acids selected from the group consisting of acrylic, methacrylic, cinnamic, crotonic, and vinylbenzoic acid, or N,N'-methylenebisacrylamide, N,N'-(1,2-dihydroxyethylene)bisacrylamide, and polyethyleneglycol diacrylate, or a mixture thereof;

C is a biological macromolecule selected from the group consisting of oligonucleotide, nucleic acid, or protein bearing an active group including an amino- or sulfhydryl group;

D is a medium for performing the polymerizing immobilization;

E is a polar or non-polar solvent;

F is a compound for promoting photo- or chemical initiated radical polymerization selected from the group consisting of ammonium persulfate, potassium persulfate, hydrogen peroxide, methylene blue, fluorescein, N,N,N',N'-tetramethylethylenediamine, 4-(N,N-dimethylamino)pyridine, triethylamine, and acetone;

a, b, c, d, e, and f are percentages (X) of each ingredient in the composition wherein for solids X equals m/v×100% and for liquids X equals v/v×100%;

wherein the total amount of monomer A and cross-linking agent B is within the range of 3-40% ($3 \leq a+b \leq 40\%$), wherein the monomer to cross-linking agent ratio being within the range of 97:3-60:40 ($3 \leq [b/(a+b)] \leq 40\%$); and percentages of ingredients C, D, E, and F being within the ranges $0 \leq c \leq 10\%$, $0 \leq d \leq 95\%$; $0 \leq e \leq 95\%$, and $0 \leq f \leq 90\%$.

3. The method according to claim 1 wherein the polymerization is performed under conditions suitable for addition or substitution reactions.

4. The method according to claim 1 wherein the polymerization comprises photo- or chemical initiated polymerization.

5. The method according to claim 2, wherein polymer is obtained by polymerization of a mixture of A+B wherein A is selected from the group consisting of acrylamide, methacrylamide, and N-[tris(hydroxymethyl)methyl]acrylamide, and B is selected from the group consisting of N,N'-methylenebisacrylamide, N,N'-(1,2-dihydroxyethylene)bisacrylamide, and polyethyleneglycol diacrylate.

6. The method according to claim 2, wherein the oligonucleotides which contain active groups including amino- and/or sulfhydryl groups; aminated DNA; DNA with a sulfhydryl group; or proteins are not subjected to modification before the immobilization process.

7. The method according to claim 2, wherein the immobilization of proteins is performed by sulfhydryl groups in a polymer carrier.

8. The method according to claim 2, wherein the immobilization of proteins is performed by amino-groups in a polymer carrier.

9. The method according to claim 2, wherein the immobilization of proteins is performed by aminoacids in a polymer carrier.

10. The method according to claim 6, wherein the immobilization of oligonucleotides is performed by 5'-terminal of the oligonucleotide.

11. The method according to claim 6, wherein the immobilization of oligonucleotides is performed by 3'-terminal of the oligonucleotide.

12. The method according to claim 1, wherein a polymer layer is formed and is covalently bonded to a substrate.

13. The method according to claim 1, wherein a polymer layer is formed and is not covalently bonded to a substrate.

14. The method according to claim 1, wherein a polymer layer is formed on a substrate is a three-dimensional gel.

15. The method according to claim 1, wherein a polymer layer is formed on a substrate and is a compact continuous layer.

16. The method according to claim 1, wherein polymer layer is formed on a substrate and is divided by empty spaces into several cells and each cell may comprise or not comprise an oligonucleotide, nucleic acid, and/or protein, and said oligonucleotide, nucleic acid, and/or protein being immobilized in various cells may have different nature and properties.

17. The method according to claim 16, wherein said cells form a phase being a one- or two-dimensional structure.

18. The method according to claim 1, wherein an application of the polymerization mixture on a substrate is carried out by using an automatic device equipped with one or more microdispensers.

19. The method according to claim 18, wherein said microdispensers are pin type microdispensers.

20. The method according to claim 18, wherein said microdispensers are microdispensers of a jet type.

21. The method according to claim 16, wherein before polymerization, one or more substrates including droplets of composition are held in a sealed container comprising the same composition mixture in amounts more than two times exceeding the total amount of the polymerization mixture as supported on substrates.

22. The method according to claim 16, wherein one or more substrates including supported droplets of composition, before and during polymerization, are placed into a sealed container under oxygen free inert atmosphere with a controlled humidity.

23. The method according to claim 22, wherein one or more substrates including supported droplets of composition, before and during polymerization, are placed into a sealed container which is filled with a gas selected from the group consisting of $N_2$, Ar, and $CO_2$.

24. The method according to claim 23, wherein said gas is continuously or periodically restored in the container.

25. The method according to claim 2, wherein E is selected from the group consisting of water; N,N-dimethylformamide and dimethylsulfoxide.

* * * * *

UNITED STATES PATENT AND TRADEMARK OFFICE
CERTIFICATE OF CORRECTION

| | | |
|---|---|---|
| PATENT NO. | : 7,846,656 B2 | Page 1 of 1 |
| APPLICATION NO. | : 10/450641 | |
| DATED | : December 7, 2010 | |
| INVENTOR(S) | : Andrei Darievich Mirzabekov et al. | |

It is certified that error appears in the above-identified patent and that said Letters Patent is hereby corrected as shown below:

Title page, line (73) delete "Institut Molekulyarnoi Biologii IM.V.A. Engelgardta Rossiiskoi Akademii Nauk" and insert -- UCHREZHDENIE ROSSIISKOI AKADEMII NAUK INSTITUT

MOLEKULYARNOI BIOLOGII IM. V.A. ENGELGARDTA RAN (IMB RAN) --

Signed and Sealed this

Fifteenth Day of February, 2011

David J. Kappos
*Director of the United States Patent and Trademark Office*